United States Patent
May et al.

(10) Patent No.: US 11,768,190 B2
(45) Date of Patent: Sep. 26, 2023

(54) DETECTING AMINE-BASED INHIBITORS IN DRILLING FLUIDS

(71) Applicant: Halliburton Energy Services, Inc., Houston, TX (US)

(72) Inventors: Preston Andrew May, Porter, TX (US); Jay Paul Deville, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 581 days.

(21) Appl. No.: 16/753,939

(22) PCT Filed: May 14, 2019

(86) PCT No.: PCT/US2019/032231
§ 371 (c)(1),
(2) Date: Apr. 6, 2020

(87) PCT Pub. No.: WO2020/231410
PCT Pub. Date: Nov. 19, 2020

(65) Prior Publication Data
US 2021/0405017 A1    Dec. 30, 2021

(51) Int. Cl.
*G01N 33/28* (2006.01)
*G01N 1/40* (2006.01)
(Continued)

(52) U.S. Cl.
CPC ....... *G01N 33/2823* (2013.01); *G01N 1/4077* (2013.01); *G01N 1/10* (2013.01);
(Continued)

(58) Field of Classification Search
CPC .... G01N 33/2823; G01N 1/4077; G01N 1/10; G01N 1/38; G01N 1/4044; G01N 31/02; E21B 49/08
See application file for complete search history.

(56) References Cited

U.S. PATENT DOCUMENTS 6,171,503 B1   1/2001   Cameron et al.
6,194,216 B1   2/2001   Walker et al.
(Continued)

FOREIGN PATENT DOCUMENTS

JP    S5544903 A      3/1980
JP    H02254191 A    10/1990
KR    20140093486 A   7/2014

OTHER PUBLICATIONS

Appleton et al., "A Chemical Method for the Determination of Free Choline in Plasma", The Journal of Biological Chemistry, vol. 205, No. 2, Dec. 1, 1953, pp. 803-813.
Harbison et al., "Improved Method for the Synthesis of Phosphatidylcholines", Notes on Methodology, Journal of Lipid Research, vol. 25, No. 10, Oct. 1984, pp. 1140-1142.
(Continued)

*Primary Examiner* — David Z Huang
(74) *Attorney, Agent, or Firm* — Kilpatrick Townsend & Stockton LLP

(57) ABSTRACT

Described herein are methods to determine an amount of shale inhibitor in drilling fluids used in wellbore operations. In some cases, methods include receiving a sample of a drilling fluid, removing solids from the sample to produce a solids-free fluid, contacting the solids-free fluid with an anion to produce a precipitate in a test solution, and determining an amount of an amine-based shale inhibitor within the sample by measuring the amount of the precipitate in the test solution.

19 Claims, 6 Drawing Sheets

(51) Int. Cl.
  *G01N 1/10* (2006.01)
  *G01N 1/38* (2006.01)
  *G01N 31/02* (2006.01)

(52) U.S. Cl.
  CPC ............. *G01N 1/38* (2013.01); *G01N 1/4044* (2013.01); *G01N 31/02* (2013.01)

(56) References Cited

U.S. PATENT DOCUMENTS

| | | | |
|---|---|---|---|
| 2004/0098202 A1* | 5/2004 | McNeil, III | G01N 33/2823 702/6 |
| 2008/0039345 A1 | 2/2008 | Kippie et al. | |
| 2010/0305010 A1 | 12/2010 | Falana et al. | |
| 2012/0190893 A1* | 7/2012 | Tian | C07C 217/28 585/4 |
| 2014/0116708 A1 | 5/2014 | Wadekar et al. | |
| 2015/0198037 A1* | 7/2015 | Van Hal | G01N 33/20 702/22 |
| 2015/0203738 A1 | 7/2015 | Witham et al. | |
| 2016/0349186 A1 | 12/2016 | Locklear et al. | |
| 2017/0122080 A1* | 5/2017 | Bertani | E21B 49/08 |

OTHER PUBLICATIONS

International Application No. PCT/US2019/032231, "International Search Report and Written Opinion", dated Feb. 13, 2020, 9 pages.
"Drilling Fluids Reference Manual", Baker Hughes Drilling Fluids Available Online at : https://www.researchgate.net/file.PostFileLoader. html?id-5733bd33615e2775127a46b7&assetKey- AS:360698208112640@1463008562446, Aug. 9, 2022, 775 Pages.
AU2019445954, "First Examination Report", dated Aug. 9, 2022, 3 pages.
Australian Patent Office, Second Examination Report, AU2019445954, dated Feb. 21, 2023, 4 pages.
Crane, Identification of Amines as Tetraphenylborates, 1956, Analytical Chemistry vol. 28, No. 11, pp. 1794-1797.
Wikipedia, Sodium Tetraphenylborate, Mar. 9, 2019, https://en. wikipedia.org/w/index.php?title=Sodium_tetraphenylborate&oldid= 886988860, 3 pages.
Baker Hughes, "Drilling Fluids Reference Manual", 2006. See especially pp. 3-103 to 3-104. Available online at https://www. researchgate.net/post/Mud-Weight-Window-Determination#view= 5733bd336 | 5e2775 I27a46b7 [accessed Nov. 16, 2022].
Great Britain Second Office Action, GB2114097.5. dated Feb. 24, 2023, 6 pages.

* cited by examiner

DETECTING AMINE-BASED INHIBITORS IN DRILLING FLUIDS

FIELD

The present disclosure relates generally to test methods for drilling fluids used in wellbore operations. More specifically, but not by way of limitation, this disclosure relates to determining an amount of shale inhibitor in drilling fluids used in wellbore operations.

BACKGROUND

Plugging a wellbore may slow or cease production from a well. Drilling fluids used in wellbore operations may include chemical additives to maintain, restore, or enhance the productivity of a well. The ability to determine drilling fluid compositions at the rig-site remains a challenge despite decades of drilling wells. Drilling fluids are generally complex compositions that change during active drilling. Solids can build up, additives may be depleted, and shear degradation can occur during drilling operations.

During drilling operations, a water-based drilling fluid is often used. Shale formations, which include clay and silt-sized particles in thin layers, are prone to plugging during drilling operations. Clay in a shale formation wellbore can absorb water from the drilling fluid and swell in reaction to contact with the water-based fluid. Shale inhibitors can prevent the migration or swelling of clay particles and minimize or prevent plugging of the wellbore, allowing the productivity of the well to be maintained or enhanced. Ramifications of poor shale inhibition can include wellbore instability, hole washout, poor solids integrity, bit balling, and/or dispersion of clay particles into the drilling fluid leading to high fluid viscosity. In reservoir sections, the swelling and migration of clays can lead to pore blocking which can impede productivity. Drilling fluids may have a predetermined initial concentration of shale inhibitors to prevent plugging issues. As the wellbore is drilled, the composition of the drilling fluid can change. The inability to determine shale inhibitor concentrations in a drilling fluid contemporaneously to drilling can impair operational reliability, such as while drilling highly reactive shale formations.

DETAILED DESCRIPTION

Figure 1:
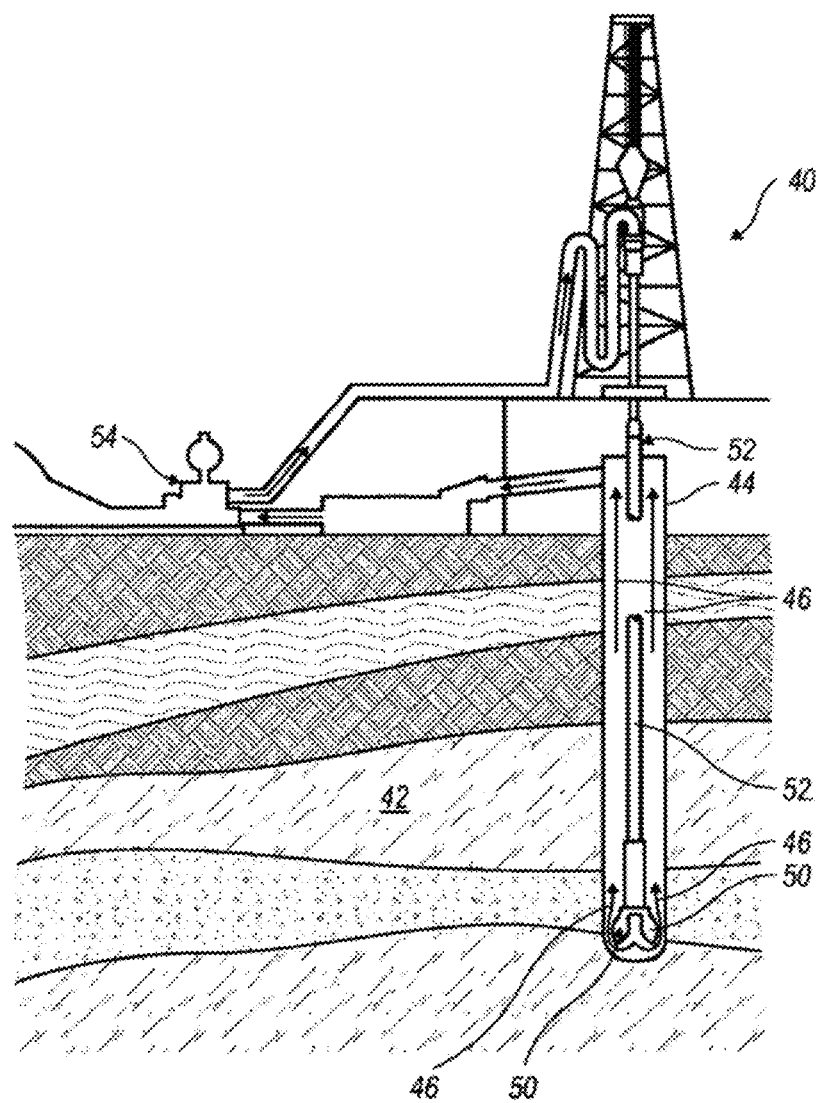
FIG. 1 is an illustrative schematic of a drilling assembly using a drilling fluid according to one example of the present disclosure.

Certain aspects and features of the present disclosure relate to methods of determining an amount of an amine-based shale inhibitor within a drilling fluid used in wellbore operations. The inhibitor may be at least one of a quaternary ammonium-based inhibitor, a tertiary amine-based inhibitor, a secondary amine-based inhibitor, or a primary amine-based inhibitor. The methods may include removing solids from a sample of drilling fluid to produce a solids-free fluid, contacting the solids-free fluid with an anion to produce a precipitate in a test solution, and determining an amount of an amine-based shale inhibitor within the sample by measuring the amount of the precipitate in the test solution. In some examples, measuring the amount of the precipitate may be performed by turbidity analysis of the test solution by means of light transmission or light scattering, by gravimetric weight analysis of the precipitate, or by volumetric analysis of the precipitate. The anion may include a borate salt or Reinecke salt. The anion may include tetraphenylborate. The amine-based shale inhibitor may comprise a quaternary ammonium-based inhibitor.

Shale inhibitors may include salts such as potassium chloride and/or quaternary ammonium salts. Shale inhibitors or stabilizers can become depleted during wellbore operations as the inhibitor reacts with the clay platelets in a wellbore. Through periodic monitoring, the concentration of inhibitor can be monitored and maintained at a target range to reduce or eliminate plugging of a wellbore and increase operational reliability. Shale inhibitors can be added to a drilling fluid when a minimum threshold concentration of inhibitor is detected to maintain operation of a wellbore that includes shale formations. Described herein are methods, both qualitative and quantitative, that can determine a concentration of amine-based shale inhibitor in a drilling fluid based on selective precipitation.

Quaternary ammonium-based cations, such as choline, can be precipitated from solution using anionic compounds. The anion used to precipitate a quaternary ammonium-based cation may be a borate salt. The anion may be tetraphenylborate. The anion may be Reinecke salt. Tertiary, secondary, or primary amine-based compounds may be protonated in a test solution and precipitated from solution using the anionic compounds.

In some examples, the methods include receiving a sample of drilling fluid. The sample may be obtained from a wellbore operation. The drilling fluid may include water, a brine, or a hydrocarbon fluid. The water may be fresh water, seawater, or salt water, for example. The hydrocarbon fluid may be mineral oils, biodegradable esters, olefins, or other variants.

The methods may include removing solids from a sample of drilling fluid to produce a solids-free fluid. In some examples, the solids-free is contacted with an anion to produce a precipitate in a test solution. The precipitate may be formed from a quaternary ammonium-based cation and an anion. The precipitate may be formed from a choline cation and an anion. The precipitate may be formed from a choline cation and tetraphenylborate. The precipitate may be formed from a choline cation and Reinecke salt. The solids can be removed by filtration to produce a filtrate. In other examples, the solids can be removed by centrifugation, simple settling, or dissolution.

The test solution, a fluid suspension containing the precipitate, can be analyzed to determine the amount of precipitate formed. In some examples, the test solution is analyzed using a turbidity meter to measure the amount of precipitate in the test solution and determine the amount of ammonium-based cation that was present in the sample of drilling fluid. In other examples, the test solution can be filtered and the precipitate dried and weighed to measure the amount of precipitate in the test solution and determine the amount of ammonium-based cation that was present in the sample of drilling fluid. In other examples, the solids can be allowed to settle in a graduated vessel and the volume of precipitate formed measured to determine the amount of ammonium-based cation that was present in the sample of drilling fluid.

In some examples, the sample of drilling fluid is diluted prior to testing. The solids-free fluid may be diluted prior to contact with the anion. The test solution may be diluted prior to measuring the amount of precipitate formed. In some examples, the sample of drilling fluid may be concentrated prior to testing. The solids-free fluid may be stripped prior to measuring the amount of precipitate formed. The concentration of precipitate in the test solution may be optimized for the method used for determining the amount of ammonium-based cation present in the sample of drilling fluid.

A concentration of quaternary ammonium-based shale inhibitor in the drilling fluid may be adjusted based on the amount of the precipitate in the test solution. The methods described herein may be performed in the field at the site of the wellbore. The methods described herein may be automated. In certain examples, the methods are performed by equipment without human interaction.

Optionally, the step of removing solids from the sample may include steps to remove potentially interfering cations. The step of removing solids from the sample may include removing solids from the sample to produce an initial solids-free fluid, contacting the initial solids-free fluid with a compound to produce an initial precipitate in an initial test solution, and removing the initial precipitate from the initial test solution to produce the solids-free fluid for further analysis. The initial solids-free fluid may be contacted with sodium perchlorate to produce an initial precipitate in an initial test solution. The solids may be removed by filtration, centrifugation, simple settling, or dissolution.

In some examples, a drilling fluid includes a potassium-containing shale inhibitor and amine-based shale inhibitor. A drilling fluid can include a potassium-containing shale inhibitor and a quaternary ammonium-based shale inhibitor. The amount of potassium within the sample of drilling fluid may be determined by measuring the amount of the initial precipitate in the initial test solution. The initial test solution, a fluid suspension containing the initial precipitate, can be analyzed to determine the amount of initial precipitate formed. The initial test solution can be analyzed using a turbidity meter to measure the amount of initial precipitate in the test solution and determine the amount of potassium cation that was present in the sample of drilling fluid. In other examples, the initial test solution can be filtered and the initial precipitate dried and weighed to measure the amount of initial precipitate in the initial test solution and determine the amount of potassium cation that was present in the sample of drilling fluid. In other examples, the initial precipitate can be allowed to settle in a graduated vessel and the volume of initial precipitate formed measured to determine the amount of potassium cation that was present in the sample of drilling fluid.

In certain examples, a concentration of potassium-based shale inhibitor in the drilling fluid may be adjusted based on the amount of the initial precipitate in the initial test solution.

Optionally, the pH of the initial test solution may be adjusted to about 2 to about 13. Some amines used on drilling fluids may be pH dependent while other amines may not be pH dependent. For example, a permanent quaternary ammonium compound that has overall positive charge may not be dependent on pH, whereas a primary, secondary, or tertiary neutral amine may be pH dependent. In a neutral state, the amine may not precipitate. Below a pKa value of a particular compound, the amine may be cationic and it may precipitate. Other amine compounds may be zwitterions such as betaines and amino acids. In some examples, these types of compounds can exist in all the charge states, when considering the net charge on the whole molecule. The amine may be treated with acid to protonate the molecule to a cationic state. The pH may be adjusted by adding hydrochloric acid or an acid known to those skilled in the art to the initial test solution. Once protonated, the amine may precipitate with the anion. In some cases, the pH may need to be decreased. The pH may be adjusted by adding sodium hydroxide or a base known to those skilled in the art to the initial test solution.

Turning to the figures, FIG. 1 illustrates a wellbore 44 being drilled through a subterranean formation 42. A drill rig 40 can be used for drilling the wellbore 44. A drill bit 50 may be mounted on the end of a drill string 52 that includes multiple sections of drill pipe. The wellbore 44 may be drilled by using a rotary drive at the surface to rotate the drill string 52 and to apply torque and force to cause the drill bit 50 to extend through wellbore 44. A drilling fluid may be displaced through the drill string 52 using one or more pumps 54. The drilling fluid may be circulated past the drill bit 50 and returned to the surface through the annulus of wellbore 44, as indicated by arrows 46, thereby removing drill cuttings (e.g., material such as rock generated by the drilling) from the wellbore 44. A shale inhibitor can be added to the drilling fluid. Although not shown, additional conduits besides drill string 52 may also be disposed within wellbore 44.

In some cases, methods to determine an amount of an amine-based shale inhibitor in a drilling fluid includes adding an anion in an amount known to be in excess of the amine-based shale inhibitor present in the drilling fluid. The amine-based shale inhibitor may be a ammonium salt. The excess anion will consume the ammonium salt present and form a maximum amount of precipitate in the test solution. The test solution may be diluted prior to determining the amount of precipitate formed.

Figure 2:
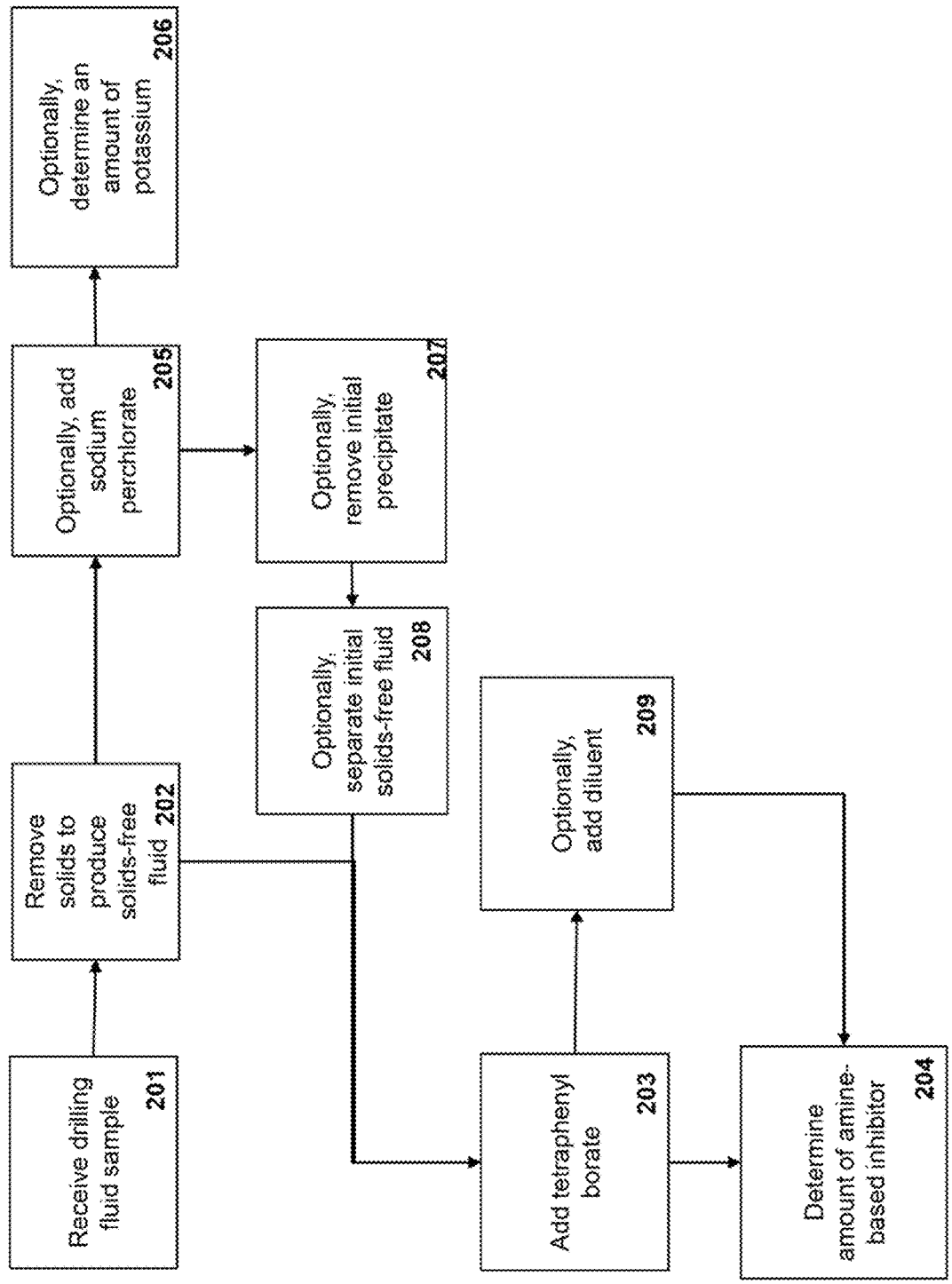
FIG. 2 is a flow chart of a method of determining an amount of an amine-based shale inhibitor within a drilling fluid according to one example of the present disclosure.

FIG. 2 shows a method to determine an amount of amine-based shale inhibitor according to one example of the present disclosure. In block 201, a sample of a drilling fluid is received. In block 202, the solids can be removed from the sample to produce a solids-free fluid. The solids can be removed from the drilling fluid sample using any suitable device and method. Examples of suitable devices and methods include filtration, centrifugation, simple settling, or dissolution. Testing may be conducted on at least a portion of the solids-free fluid. In block 205, sodium perchlorate can optionally be added to the solids-free fluid to form an initial precipitate with potassium ions to form an initial test solution from the solids-free drilling fluid sample. In block 206, the initial test solution can be analyzed for potassium content by measuring the amount of precipitate formed in the initial test solution. The precipitate can be measured using methods known to those in the art. Examples of analysis include turbidity and gravimetric weight analysis. The measured amount of initial precipitate can be compared to known values and concentration of potassium. In block 207, the initial precipitate can be removed from the initial test solution. The initial precipitate can be removed using any suitable device and method. Examples of suitable devices and methods include filtration or centrifugation.

Optionally, a portion of the initial solids-free fluid can be separated for testing as shown in block 208 for further analysis. In block 203, at least a portion of the solids-free fluid or initial solids-free fluid may be contacted with tetraphenylborate to form a precipitate in a concentrated solution test solution. In block 209, a diluent, such as water, can optionally be added to the concentrated solution. In block 204, the level of precipitate in the test solution can be measured and compared to known values of turbidity and concentration of ammonium salt. The precipitate can be measured using methods known to those in the art. Examples of analysis include turbidity and gravimetric weight analysis.

Figure 3:
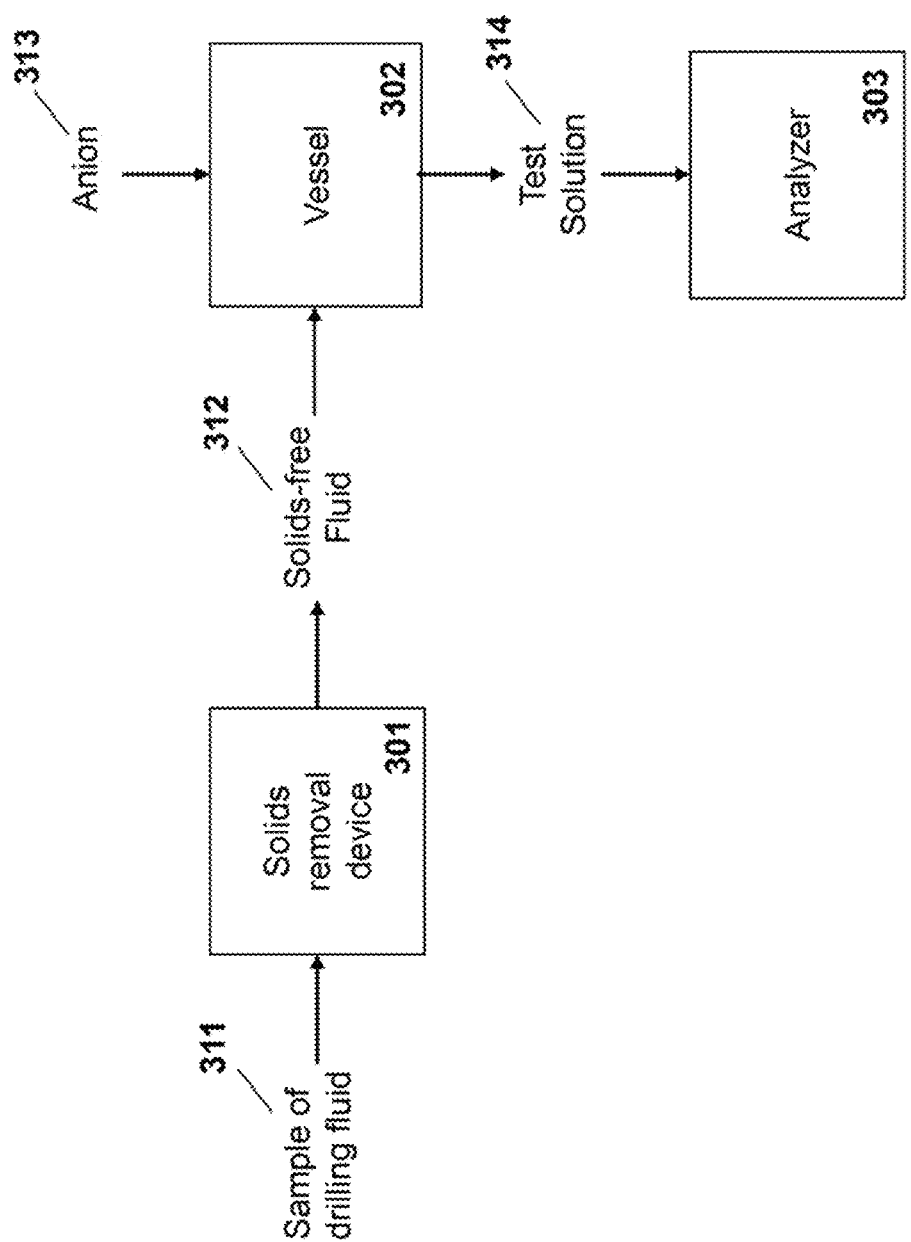
FIG. 3 is a block diagram of a system for determining an amount of an amine-based shale inhibitor within a drilling fluid according to one example of the present disclosure.

In some cases, systems to determine an amount of an amine-based shale inhibitor in a drilling fluid may be configured. FIG. 3 shows a system to determine an amount of an ammonium-based shale inhibitor according to one example of the present disclosure. A solids removal device 301 may remove solids from a sample of a drilling fluid 311 to produce a solids-free fluid 312. A vessel 302 may receive at least a portion of the solids-free fluid 312 and an anion 313 and contain the test solution 314. An analyzer 303 may determine an amount of an ammonium-based shale inhibitor within the test solution 314. Examples of a solids removal device include a filter and a centrifuge. A system to determine an amount of an ammonium-based shale inhibitor in a drilling fluid can include a turbidity meter to determine an amount of a quaternary ammonium-based shale inhibitor within the solids-free fluid. The system may use a borate salt or Reinecke salt as the anion.

In some cases, an apparatus to determine an amount of an ammonium-based shale inhibitor in a drilling fluid includes an analyzer to measure an amount of a precipitate formed in a test solution from a sample of drilling fluid having the solids removed, where the precipitate is formed by an ammonium-based shale inhibitor contacted with an anion. The anion may be a borate salt or Reinecke salt. The drilling fluid may include water, brine, or a hydrocarbon fluid. The amine-based shale inhibitor may be at least one of a quaternary ammonium-based inhibitor, a tertiary amine-based inhibitor, a secondary amine-based inhibitor, or a primary amine-based inhibitor.

EXAMPLES

Example 1

Increasing Turbidity

Figure 4:
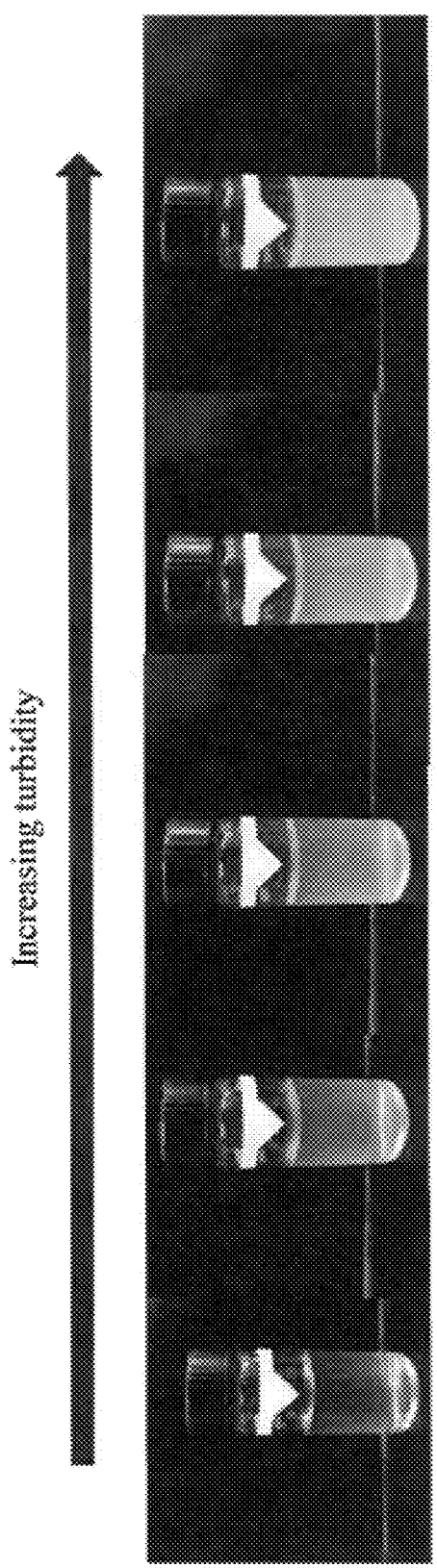
FIG. 4 is a depiction of samples with various amounts of precipitate formed in a test solution according to one example of the present disclosure.

Samples of a choline chloride solution were prepared by adding one mL of aqueous choline chloride solution (five lb/bbl) to ten mL of deionized water. Increasing amounts of sodium tetraphenylborate solution (0.5% aqueous solution) were added to the choline chloride solution. FIG. 4 shows the increasing level of precipitate formed and increasing level of turbidity observed in the samples with increased amounts of sodium tetraphenylborate solution.

Example 2

Turbidity Measurements

Figure 5:
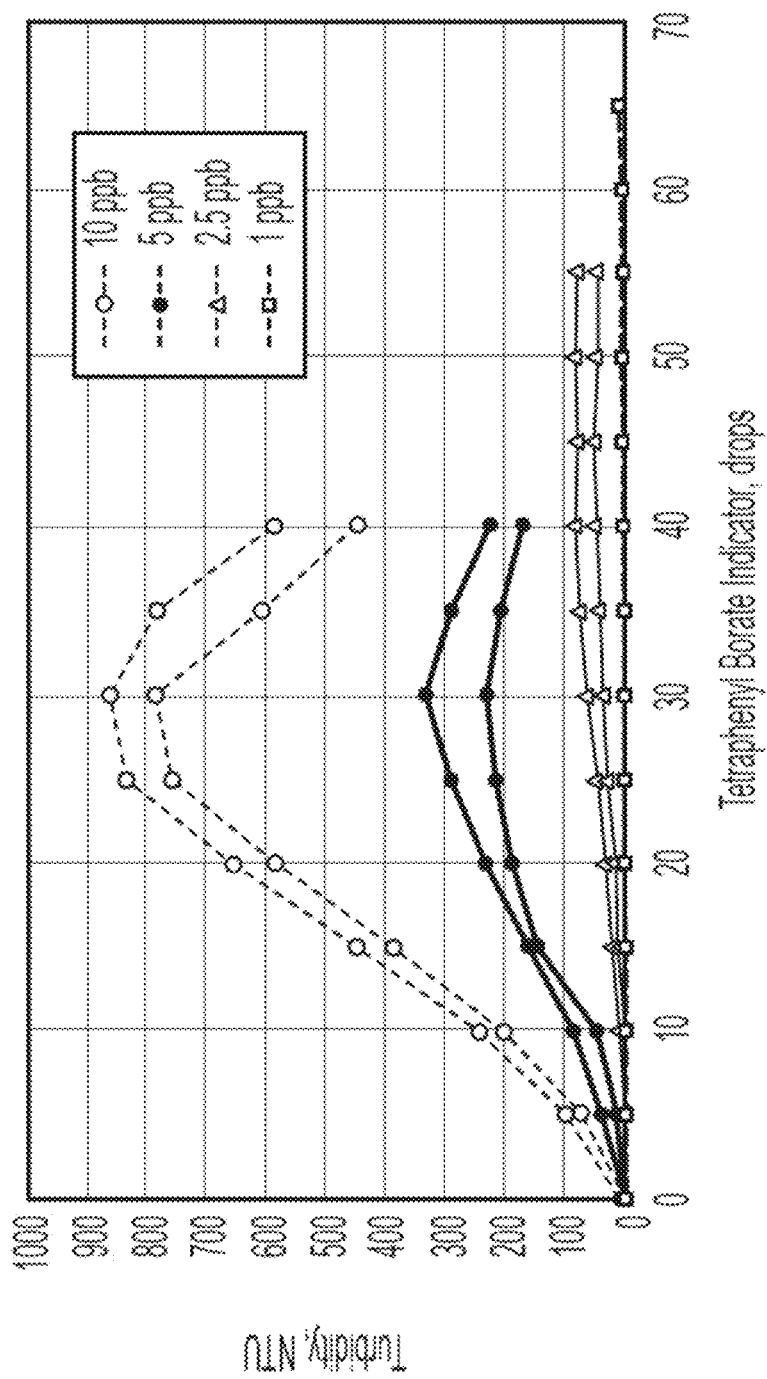
FIG. 5 is a chart of turbidity with respect to volume of tetraphenylborate, obtained from turbidity testing according to one example of the present disclosure.
Figure 6:
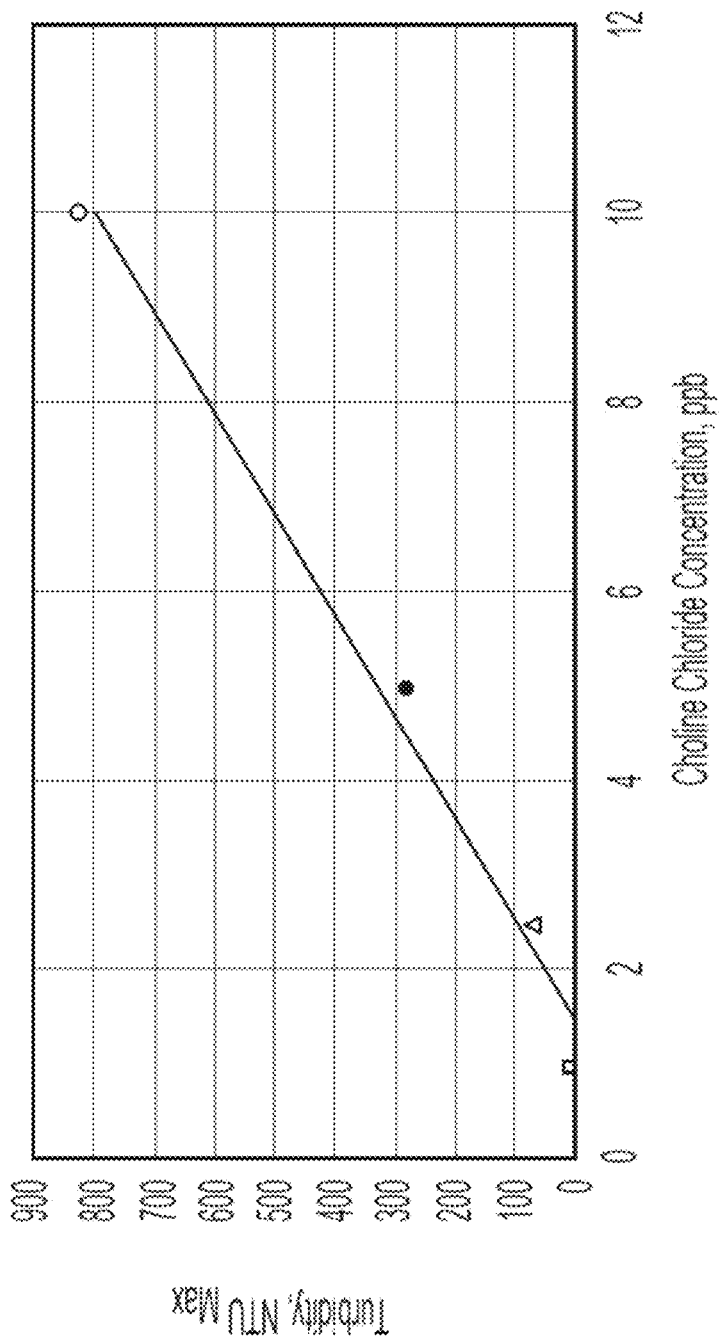
FIG. 6 is a chart of maximum turbidity with respect to choline chloride concentration, obtained from turbidity testing according to one example of the present disclosure.

Four samples of a choline chloride solution in deionized water were prepared, each with a different concentration (1 lb/bbl, 2.5 lb/bbl, 5 lb/bbl, and 10 lb/bbl). One drop of each solution was diluted with ten mL of deionized water. Each sample was titrated with a sodium tetraphenylborate solution (0.5% aqueous solution) in a dropwise manner. The turbidity of each sample was measured at an initial concentration and after each addition of 5 drops. A maximum turbidity value ($NTU_{max}$) was determined for each sample. The turbidity was observed to increase to $NTU_{max}$ and thereafter the turbidity was observed to decease as additional sodium tetraphenylborate solution was added to the sample. FIG. 5 shows the turbidity measurements for each sample of choline. FIG. 6 shows a plot of $NTU_{max}$ values versus choline chloride concentration, which can be used to determine choline chloride concentration from turbidity measurements on samples of drilling fluids.

Illustrative Embodiments of Suitable Fluids and Methods

As used below, any reference to methods, products, or systems is understood as a reference to each of those methods, products, or systems disjunctively (e.g., "Illustrative embodiment 1-4 is understood as illustrative embodiment 1, 2, 3, or 4.").

Illustrative embodiment 1 is a method comprising receiving a sample of a drilling fluid, removing solids from the sample to produce a solids-free fluid, contacting the solids-free fluid with an anion to produce a precipitate in a test solution, and determining an amount of an amine-based shale inhibitor within the sample by measuring the amount of the precipitate in the test solution.

Illustrative embodiment 2 is the method of any preceding or subsequent illustrative embodiment, wherein measuring the amount of the precipitate is performed by turbidity analysis of the test solution, by gravimetric weight analysis of the precipitate, or by volumetric analysis of the precipitate.

Illustrative embodiment 3 is the method of any preceding or subsequent illustrative embodiment, wherein the amine-based shale inhibitor comprises at least one of a quaternary ammonium-based inhibitor, a tertiary amine-based inhibitor, a secondary amine-based inhibitor, or a primary amine-based inhibitor.

Illustrative embodiment 4 is the method of any preceding or subsequent illustrative embodiment, wherein the anion comprises a borate salt or Reinecke salt.

Illustrative embodiment 5 is the method of any preceding or subsequent illustrative embodiment, wherein the anion comprises tetraphenylborate.

Illustrative embodiment 6 is the method of any preceding or subsequent illustrative embodiment, wherein the drilling fluid comprises water, brine, or a hydrocarbon fluid.

Illustrative embodiment 7 is the method of any preceding or subsequent illustrative embodiment, wherein the sample is obtained from a wellbore operation.

Illustrative embodiment 8 is the method of any preceding or subsequent illustrative embodiment, further comprising adjusting a concentration of the amine-based shale inhibitor in the drilling fluid based on a measured amount of the precipitate in the test solution.

Illustrative embodiment 9 is the method of any preceding or subsequent illustrative embodiment, wherein removing solids from the sample to produce the solids-free fluid comprises removing solids from the sample to produce an initial solids-free fluid, contacting the initial solids-free fluid with sodium perchlorate to produce an initial precipitate in an initial test solution, and removing the initial precipitate from the initial test solution to produce the solids-free fluid.

Illustrative embodiment 10 is the method of illustrative embodiment 9, further comprising determining an amount of potassium within the sample by measuring the amount of the initial precipitate in the initial test solution.

Illustrative embodiment 11 is the method illustrative embodiment 10, wherein measuring the amount of the initial precipitate is performed by turbidity analysis of the initial test solution, by gravimetric weight of the initial precipitate, or by volumetric analysis of the initial precipitate.

Illustrative embodiment 12 is the method of illustrative embodiment 10 or 11, further comprising adjusting a concentration of potassium in the drilling fluid based on a measured amount of the precipitate in the initial test solution.

Illustrative embodiment 13 is the method of any one of illustrative embodiments 9-12, further comprising adjusting a pH of the initial test solution to between 2 and 13.

Illustrative embodiment 14 is the method of any preceding or subsequent illustrative embodiment, further comprising diluting the test solution prior to measuring the amount of the precipitate.

Illustrative embodiment 15 is a system comprising a solids removal device to remove solids from a sample of a drilling fluid to produce a solids-free fluid, a vessel to receive at least a portion of the solids-free fluid and an anion, and an analyzer to determine an amount of an amine-based shale inhibitor within the solids-free fluid.

Illustrative embodiment 16 is the system of any preceding or subsequent illustrative embodiment, wherein the analyzer is a turbidity meter.

Illustrative embodiment 17 is the system of any preceding or subsequent illustrative embodiment, wherein the anion comprises a borate salt or Reinecke salt.

Illustrative embodiment 18 is an apparatus comprising an analyzer to measure an amount of a precipitate formed from a solids-free sample of drilling fluid that includes an amine-based shale inhibitor contacted with an anion.

Illustrative embodiment 19 is the apparatus of any preceding or subsequent illustrative embodiment, wherein the anion comprises a borate salt or Reinecke salt.

Illustrative embodiment 20 is the method of any preceding or subsequent illustrative embodiment, wherein the amine-based shale inhibitor comprises at least one of a quaternary ammonium-based inhibitor, a tertiary amine-based inhibitor, a secondary amine-based inhibitor, or a primary amine-based inhibitor.

DEFINITIONS AND DESCRIPTIONS

The terms "disclosure," "the disclosure," "the present disclosure," "embodiment," "certain embodiment" and the like are used herein are intended to refer broadly to all the subject matter of this patent application and the claims below. Statements containing these terms should be understood not to limit the subject matter described herein or to limit the meaning or scope of the patent claims below. The terms "comprising," "having," "including," and "containing" are to be construed as open-ended terms (i.e., meaning "including, but not limited to") unless otherwise noted. It is further noted that, as used in this specification, the singular forms "a," "an," and "the" include plural referents unless expressly and unequivocally limited to one referent.

Various embodiments of the present disclosure have been described herein. It should be recognized that these embodiments are merely illustrative of the present disclosure. Variations of those preferred embodiments may become apparent to those of ordinary skill in the art upon reading the foregoing description. The inventors expect skilled artisans to employ such variations as appropriate, and the inventors intend for the present disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated or otherwise clearly contradicted by context.

What is claimed is:

1. A method comprising:
receiving a sample of a drilling fluid;
removing solids from the sample to produce a solids-free fluid, wherein removing solids from the sample to produce the solids-free fluid comprises:
removing solids from the sample to produce an initial solids-free fluid;
contacting the initial solids-free fluid with sodium perchlorate to produce an initial precipitate in an initial test solution; and
removing the initial precipitate from the initial test solution to produce the solids-free fluid;
contacting the solids-free fluid with an anion to produce a precipitate in a test solution; and
determining an amount of an amine-based shale inhibitor within the sample by measuring an amount of the precipitate in the test solution.

2. The method of claim 1, wherein measuring the amount of the precipitate is performed by turbidity analysis of the test solution, by gravimetric weight analysis of the precipitate, or by volumetric analysis of the precipitate.

3. The method of claim 1, wherein the amine-based shale inhibitor comprises at least one of a quaternary ammonium-based inhibitor, a tertiary amine-based inhibitor, a secondary amine-based inhibitor, or a primary amine-based inhibitor.

4. The method of claim 1, wherein the anion comprises a borate salt or Reinecke salt.

5. The method of claim 1, wherein the anion comprises tetraphenylborate.

6. The method of claim 1, wherein the drilling fluid comprises water, brine, or a hydrocarbon fluid.

7. The method of claim 1, wherein the sample is obtained from a wellbore operation.

8. The method of claim 1, further comprising adjusting a concentration of the amine-based shale inhibitor in the drilling fluid based on a measured amount of the precipitate in the test solution.

9. The method of claim 1, further comprising determining an amount of potassium within the sample by measuring the amount of the initial precipitate in the initial test solution.

10. The method of claim 9, wherein measuring the amount of the initial precipitate is performed by turbidity analysis of the initial test solution, by gravimetric weight of the initial precipitate, or by volumetric analysis of the initial precipitate.

11. The method of claim 9, further comprising adjusting a concentration of potassium in the drilling fluid based on a measured amount of the precipitate in the initial test solution.

12. The method of claim 1, further comprising adjusting a pH of the initial test solution to between 2 and 13.

13. The method of claim 1, further comprising diluting the test solution prior to measuring the amount of the precipitate.

14. A system comprising:
   a solids removal device configured to remove solids from a sample of a drilling fluid to produce a solids-free fluid by:
      removing solids from the sample to produce an initial solids-free fluid;
      contacting the initial solids-free fluid with sodium perchlorate to produce an initial precipitate in an initial test solution; and
      removing the initial precipitate from the initial test solution to produce the solids-free fluid;
   a vessel configured to receive at least a portion of the solids-free fluid and an anion and collect a precipitate produced upon contacting the solids-free fluid with the anion; and
   an analyzer configured to determine an amount of an amine-based shale inhibitor within the solids-free fluid by measuring an amount of the precipitate.

15. The system of claim 14, wherein the analyzer is a turbidity meter.

16. The system of claim 14, wherein the anion comprises a borate salt or Reinecke salt.

17. An apparatus comprising:
   an analyzer configured to determine an amount of an amine-based shale inhibitor in a solid-free sample of drilling fluid by measuring an amount of a precipitate produced upon contacting the solids-free sample of drilling fluid with an anion, wherein a solids removal device is configured to prepare the solid-free sample by:
      removing solids from a sample to produce an initial solids-free fluid;
      contacting the initial solids-free fluid with sodium perchlorate to produce an initial precipitate in an initial test solution; and
   removing the initial precipitate from the initial test solution to produce the solid-free sample.

18. The apparatus of claim 17, wherein the anion comprises a borate salt or Reinecke salt.

19. The apparatus of claim 17, wherein the amine-based shale inhibitor comprises at least one of a quaternary ammonium-based inhibitor, a tertiary amine-based inhibitor, a secondary amine-based inhibitor, or a primary amine-based inhibitor.

* * * * *